US010501763B2

(12) United States Patent
Bae et al.

(10) Patent No.: US 10,501,763 B2
(45) Date of Patent: Dec. 10, 2019

(54) MICROORGANISM PRODUCING O-ACETYL-HOMOSERINE AND METHOD FOR PRODUCING O-ACETYLHOMOSERINE USING THE SAME

(71) Applicant: CJ CHEILJEDANG CORPORATION, Seoul (KR)

(72) Inventors: Jee Yeon Bae, Incheon (KR); Hyun Ah Kim, Jeollabuk-do (KR); Yong Uk Shin, Gyeonggi-do (KR); So Young Kim, Gyeonggi-do (KR); Sang Kyoum Kim, Gyeonggi-do (KR); Kwang Ho Na, Seoul (KR); Ju Hee Seo, Gyeonggi-do (KR); Sung Kwang Son, Seoul (KR); Hye Ryun Yoo, Incheon (KR); Jin Geun Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/316,475

(22) PCT Filed: Jun. 5, 2015

(86) PCT No.: PCT/KR2015/005659
§ 371 (c)(1),
(2) Date: Dec. 5, 2016

(87) PCT Pub. No.: WO2015/186990
PCT Pub. Date: Dec. 10, 2015

(65) Prior Publication Data
US 2017/0137853 A1 May 18, 2017

(30) Foreign Application Priority Data
Jun. 5, 2014 (KR) .................. 10-2014-0068613

(51) Int. Cl.
*C07K 14/245* (2006.01)
*C12P 13/04* (2006.01)
*C12N 1/21* (2006.01)
*C12N 9/88* (2006.01)
*C12N 9/10* (2006.01)
*C12N 9/02* (2006.01)
*C12P 13/06* (2006.01)
*C12P 13/02* (2006.01)
*C12N 9/12* (2006.01)
*C12N 15/52* (2006.01)
*C12R 1/12* (2006.01)

(52) U.S. Cl.
CPC ........... *C12P 13/06* (2013.01); *C07K 14/245* (2013.01); *C12N 9/0008* (2013.01); *C12N 9/1029* (2013.01); *C12N 9/1096* (2013.01); *C12N 9/1205* (2013.01); *C12N 9/1217* (2013.01); *C12N 9/88* (2013.01); *C12N 15/52* (2013.01); *C12P 13/02* (2013.01); *C12Y 102/01011* (2013.01); *C12Y 203/01031* (2013.01); *C12Y 206/01001* (2013.01); *C12Y 207/01039* (2013.01); *C12Y 207/02004* (2013.01); *C12Y 401/01031* (2013.01); *C12Y 402/01022* (2013.01); *C12R 1/12* (2013.01)

(58) Field of Classification Search
None
See application file for complete search history.

(56) References Cited

U.S. PATENT DOCUMENTS

| 2007/0026505 A1* | 2/2007 | Madden ................. C07K 14/24 435/106 |
| 2009/0253186 A1 | 10/2009 | Kim et al. |
| 2009/0298135 A1 | 12/2009 | Maier et al. |
| 2010/0184164 A1* | 7/2010 | Kim ..................... C12N 9/1029 435/113 |
| 2011/0053253 A1 | 3/2011 | Kim et al. |

FOREIGN PATENT DOCUMENTS

| CN | 101356281 A | 1/2009 | |
| EP | 2 657 250 A2 | 10/2013 | |
| JP | 2004-236660 A | 8/2004 | |
| JP | 2009-501512 A | 1/2009 | |
| JP | 2009-544309 A | 12/2009 | |
| JP | 2011-045360 A | 3/2011 | |
| JP | 6375391 B2 * | 8/2018 | ............. C12P 13/06 |
| KR | 10-0905381 B1 | 6/2009 | |
| KR | 10-0951766 B1 | 3/2010 | |
| KR | 10-1117012 B1 | 2/2012 | |

(Continued)

OTHER PUBLICATIONS

Figge, Methionine Biosynthesis in *Escherichia coli* and Corynebacterium glutamicum, Microbiol. Monog., Wendisch, Ed., 5, 2006, 163-93.*
Liu et al., YjeH Is a Novel Exporter of L-Methionine and Branched-Chain Amino Acids in *Escherichia coli*, Appl. Environ. Microbiol., Aug. 2015, 81, 7753-66.*
Datsenko and Wanner, "One-step inactivation of chromosomal genes in *Escherichia coli* K-12 using PCR products," PNAS 97(12): 6640-6645, Jun. 6, 2000.

*Primary Examiner* — Robert B Mondesi
*Assistant Examiner* — Todd M Epstein
(74) *Attorney, Agent, or Firm* — Cooley LLP

(57) ABSTRACT

The present disclosure relates to a microorganism producing O-acetylhomoserine with high efficiency and a method for producing O-acetylhomoserine and L-methionine using the microorganism. The present disclosure provides a microorganism producing O-acetylhomoserine having an enhanced activity of a protein which is predicted to export O-acetylhomoserine, and a method for producing O-acetylhomoserine and L-methionine using the microorganism.

8 Claims, 1 Drawing Sheet
Specification includes a Sequence Listing.

(56) References Cited

FOREIGN PATENT DOCUMENTS

| KR | 10-1335841 B1 | 11/2013 |
|---|---|---|
| WO | WO-2006/138689 A2 | 12/2006 |
| WO | 2008/013432 A1 | 1/2008 |
| WO | 2012/087039 A2 | 6/2012 |

* cited by examiner

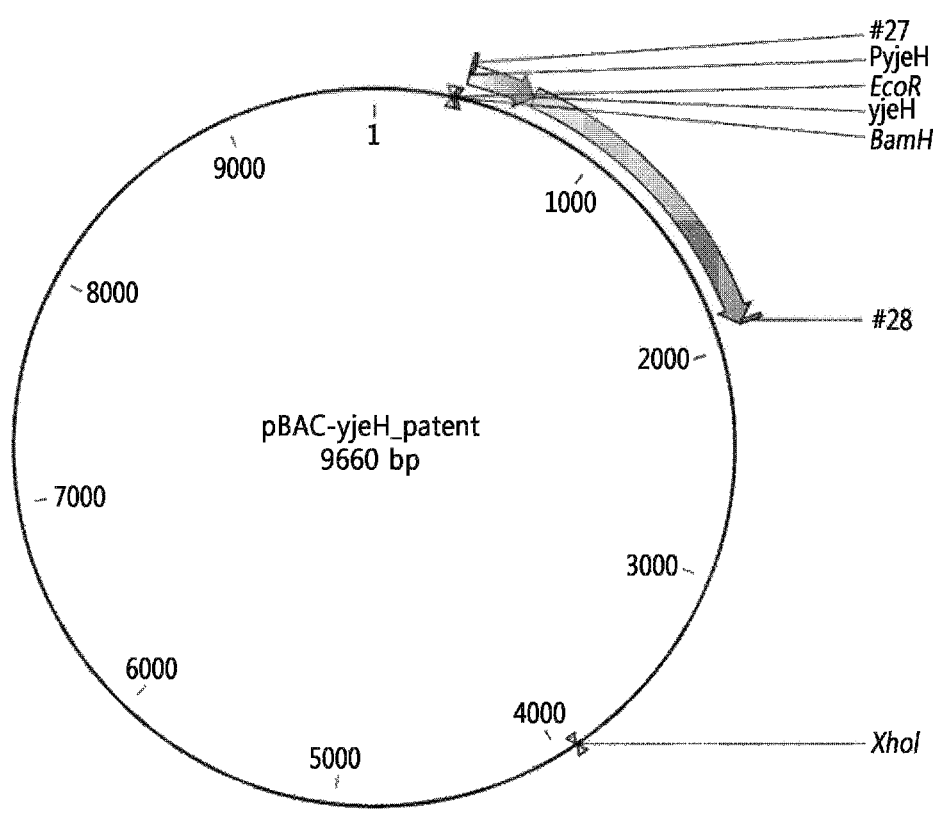

SEQUENCE LISTING

```
<160> NUMBER OF SEQ ID NOS: 53

<210> SEQ ID NO 1
<211> LENGTH: 418
<212> TYPE: PRT
<213> ORGANISM: Escherichia coli

<400> SEQUENCE: 1

Met Ser Gly Leu Lys Gln Glu Leu Gly Leu Ala Gln Gly Ile Gly Leu
1               5                   10                  15

Leu Ser Thr Ser Leu Leu Gly Thr Gly Val Phe Ala Val Pro Ala Leu
            20                  25                  30

Ala Ala Leu Val Ala Gly Asn Asn Ser Leu Trp Ala Trp Pro Val Leu
        35                  40                  45

Ile Ile Leu Val Phe Pro Ile Ala Ile Val Phe Ala Ile Leu Gly Arg
    50                  55                  60

His Tyr Pro Ser Ala Gly Gly Val Ala His Phe Val Gly Met Ala Phe
65                  70                  75                  80

Gly Ser Arg Leu Glu Arg Val Thr Gly Trp Leu Phe Leu Ser Val Ile
                85                  90                  95
```

Pro Val Gly Leu Pro Ala Ala Leu Gln Ile Ala Ala Gly Phe Gly Gln
                100                 105                 110

Ala Met Phe Gly Trp His Ser Trp Gln Leu Leu Ala Glu Leu Gly
            115                 120                 125

Thr Leu Ala Leu Val Trp Tyr Ile Gly Thr Arg Gly Ala Ser Ser Ser
    130                 135                 140

Ala Asn Leu Gln Thr Val Ile Ala Gly Leu Ile Val Ala Leu Ile Val
145                 150                 155                 160

Ala Ile Trp Trp Ala Gly Asp Ile Lys Pro Ala Asn Ile Pro Phe Pro
                165                 170                 175

Ala Pro Gly Asn Ile Glu Leu Thr Gly Leu Phe Ala Ala Leu Ser Val
            180                 185                 190

Met Phe Trp Cys Phe Val Gly Leu Glu Ala Phe Ala His Leu Ala Ser
        195                 200                 205

Glu Phe Lys Asn Pro Glu Arg Asp Phe Pro Arg Ala Leu Met Ile Gly
    210                 215                 220

Leu Leu Leu Ala Gly Leu Val Tyr Trp Gly Cys Thr Val Val Val Leu
225                 230                 235                 240

His Phe Asp Ala Tyr Gly Glu Lys Met Ala Ala Ala Ser Leu Pro
                245                 250                 255

Lys Ile Val Val Gln Leu Phe Gly Val Gly Ala Leu Trp Ile Ala Cys
            260                 265                 270

Val Ile Gly Tyr Leu Ala Cys Phe Ala Ser Leu Asn Ile Tyr Ile Gln
        275                 280                 285

Ser Phe Ala Arg Leu Val Trp Ser Gln Ala Gln His Asn Pro Asp His
    290                 295                 300

Tyr Leu Ala Arg Leu Ser Ser Arg His Ile Pro Asn Asn Ala Leu Asn
305                 310                 315                 320

Ala Val Leu Gly Cys Cys Val Val Ser Thr Leu Val Ile His Ala Leu
                325                 330                 335

Glu Ile Asn Leu Asp Ala Leu Ile Ile Tyr Ala Asn Gly Ile Phe Ile
            340                 345                 350

Met Ile Tyr Leu Leu Cys Met Leu Ala Gly Cys Lys Leu Leu Gln Gly
        355                 360                 365

Arg Tyr Arg Leu Leu Ala Val Val Gly Gly Leu Leu Cys Val Leu Leu
    370                 375                 380

Leu Ala Met Val Gly Trp Lys Ser Leu Tyr Ala Leu Ile Met Leu Ala
385                 390                 395                 400

Gly Leu Trp Leu Leu Leu Pro Lys Arg Lys Thr Pro Glu Asn Gly Ile
                405                 410                 415

Thr Thr

<210> SEQ ID NO 2
<211> LENGTH: 1257
<212> TYPE: DNA
<213> ORGANISM: Escherichia coli

<400> SEQUENCE: 2
atgagtggac tcaaacaaga actggggctg gcccagggca ttggcctgct atcgacgtca      60
ttattaggca ctggcgtgtt tgccgttcct gcgttagctg cgctggtagc gggcaataac     120
agcctgtggg cgtggcccgt tttgattatc ttagtgttcc cgattgcgat tgtgtttgcg     180
attctgggtc gccactatcc cagcgcaggc ggcgtcgcgc acttcgtcgg tatggcgttt     240

-continued

```
ggttcgcggc ttgagcgagt caccggctgg ctgtttttat cggtcattcc cgtgggtttg    300
cctgccgcac tacaaattgc cgccgggttc ggccaggcga tgtttggctg catagctgg     360
caactgttgt tggcagaact cggtacgctg gcgctggtgt ggtatatcgg tactcgcggt    420
gccagttcca gtgctaatct acaaaccgtt attgccggac ttatcgtcgc gctgattgtc    480
gctatctggt gggcgggcga tatcaaacct gcgaatatcc cctttccggc acctggtaat    540
atcgaactta ccgggttatt tgctgcgtta tcagtgatgt tctggtgttt tgtcggtctg    600
gaggcatttg cccatctcgc ctcggaattt aaaaatccag agcgtgattt tcctcgtgct    660
ttgatgattg gtctgctgct ggcaggatta gtctactggg gctgtacggt agtcgtctta    720
cacttcgacg cctatggtga aaaaatggcg gcggcagcat cgcttccaaa aattgtagtg    780
cagttgttcg gtgtaggagc gttatggatt gcctgcgtga ttggctatct ggcctgcttt    840
gccagtctca acatttatat acagagcttc gcccgcctgg tctggtcgca ggcgcaacat    900
aatcctgacc actacctggc acgcctctct tctcgccata tcccgaataa tgccctcaat    960
gcggtgctcg gctgctgtgt ggtgagcact ttggtgattc atgctttaga gatcaatctg    1020
gacgctctta ttatttatgc caatggcatc tttattatga tttatctgtt atgcatgctg    1080
gcaggctgta aattattgca aggacgttat cgactactgg cggtggttgg cgggctgtta    1140
tgcgttctgt tactggcaat ggtcggctgg aaaagtctct atgcgctgat catgctggcg    1200
gggttatggc tgttgctgcc aaaacgaaaa acgccggaaa atggcataac cacataa      1257
```

<210> SEQ ID NO 3
<211> LENGTH: 386
<212> TYPE: PRT
<213> ORGANISM: Escherichia coli

<400> SEQUENCE: 3

```
Met Thr Arg Lys Gln Ala Thr Ile Ala Val Arg Ser Gly Leu Asn Asp
1               5                   10                  15

Asp Glu Gln Tyr Gly Cys Val Val Pro Ile His Leu Ser Ser Thr
            20                  25                  30

Tyr Asn Phe Thr Gly Phe Asn Glu Pro Arg Ala His Asp Tyr Ser Arg
        35                  40                  45

Arg Gly Asn Pro Thr Arg Asp Val Val Gln Arg Ala Leu Ala Glu Leu
    50                  55                  60

Glu Gly Gly Ala Gly Ala Val Leu Thr Asn Thr Gly Met Ser Ala Ile
65                  70                  75                  80

His Leu Val Thr Thr Val Phe Leu Lys Pro Gly Asp Leu Leu Val Ala
                85                  90                  95

Pro His Asp Cys Tyr Gly Gly Ser Tyr Arg Leu Phe Asp Ser Leu Ala
            100                 105                 110

Lys Arg Gly Cys Tyr Arg Val Leu Phe Val Asp Gln Gly Asp Glu Gln
        115                 120                 125

Ala Leu Arg Ala Ala Leu Ala Glu Lys Pro Lys Leu Val Leu Val Glu
    130                 135                 140

Ser Pro Ser Asn Pro Leu Leu Arg Val Val Asp Ile Ala Lys Ile Cys
145                 150                 155                 160

His Leu Ala Arg Glu Val Gly Ala Val Ser Val Val Asp Asn Thr Phe
                165                 170                 175

Leu Ser Pro Ala Leu Gln Asn Pro Leu Ala Leu Gly Ala Asp Leu Val
            180                 185                 190

Leu His Ser Cys Thr Lys Tyr Leu Asn Gly His Ser Asp Val Val Ala
```

```
                195                 200                 205
Gly Val Val Ile Ala Lys Asp Pro Asp Val Val Thr Glu Leu Ala Trp
    210                 215                 220
Trp Ala Asn Asn Ile Gly Val Thr Gly Gly Ala Phe Asp Ser Tyr Leu
225                 230                 235                 240
Leu Leu Arg Gly Leu Arg Thr Leu Val Pro Arg Met Glu Leu Ala Gln
                245                 250                 255
Arg Asn Ala Gln Ala Ile Val Lys Tyr Leu Gln Thr Gln Pro Leu Val
                260                 265                 270
Lys Lys Leu Tyr His Pro Ser Leu Pro Glu Asn Gln Gly His Glu Ile
                275                 280                 285
Ala Ala Arg Gln Gln Lys Gly Phe Gly Ala Met Leu Ser Phe Glu Leu
                290                 295                 300
Asp Gly Asp Glu Gln Thr Leu Arg Arg Phe Leu Gly Gly Leu Ser Leu
305                 310                 315                 320
Phe Thr Leu Ala Glu Ser Leu Gly Gly Val Glu Ser Leu Ile Ser His
                325                 330                 335
Ala Ala Thr Met Thr His Ala Gly Met Ala Pro Glu Ala Arg Ala Ala
                340                 345                 350
Ala Gly Ile Ser Glu Thr Leu Leu Arg Ile Ser Thr Gly Ile Glu Asp
                355                 360                 365
Gly Glu Asp Leu Ile Ala Asp Leu Glu Asn Gly Phe Arg Ala Ala Asn
                370                 375                 380
Lys Gly
385

<210> SEQ ID NO 4
<211> LENGTH: 1161
<212> TYPE: DNA
<213> ORGANISM: Escherichia coli

<400> SEQUENCE: 4
atgacgcgta aacaggccac catcgcagtg cgtagcgggt taaatgacga cgaacagtat      60
ggttgcgttg tcccaccgat ccatctttcc agcacctata actttaccgg atttaatgaa     120
ccgcgcgcgc atgattactc gcgtcgcggc aacccaacgc gcgatgtggt tcagcgtgcg     180
ctggcagaac tggaaggtgg tgctggtgca gtacttacta ataccggcat gtccgcgatt     240
cacctggtaa cgaccgtctt tttgaaacct ggcgatctgc tggttgcgcc gcacgactgc     300
tacgccggta gctatcgcct gttcgacagt ctggcgaaac gcggttgcta tcgcgtgttg     360
tttgttgatc aaggcgatga acaggcatta cgggcagcgc tggcagaaaa acccaaactg     420
gtactggtag aaagcccaag taatccattg ttacgcgtcg tggatattgc gaaaatctgc     480
catctggcaa gggaagtcgg ggcggtgagc gtggtggata cacccttctt aagcccggca     540
ttacaaaatc cgctggcatt aggtgccgat ctggtgttgc attcatgcac gaaatatctg     600
aacggtcact cagacgtagt ggccggcgtg gtgattgcta agaccccgga cgttgtcact     660
gaactggcct ggtgggcaaa caatattggc gtgacgggcg gcgcgtttga cagctatctg     720
ctgctacgtg ggttgcgaac gctggtgccg cgtatggagc tggcgcagcg caacgcgcag     780
gcgattgtga atacctgca aacccagccg ttggtgaaaa actgtatca cccgtcgttg     840
ccggaaaatc aggggcatga aattgccgcg cgccagcaaa aaggctttgg cgcaatgttg     900
agttttgaac tggatggcga tgagcagacg ctgcgtcgtt tcctgggcgg gctgtcgttg     960
tttacgctgg cggaatcatt agggggagtg gaaagtttaa tctctcacgc cgcaaccatg    1020
```

```
acacatgcag gcatggcacc agaagcgcgt gctgccgccg ggatctccga dacgctgctg    1080
cgtatctcca ccggtattga agatggcgaa gatttaattg ccgacctgga aaatggcttc    1140
cgggctgcaa acaagggta a                                               1161
```

<210> SEQ ID NO 5
<211> LENGTH: 310
<212> TYPE: PRT
<213> ORGANISM: Escherichia coli

<400> SEQUENCE: 5

```
Met Val Lys Val Tyr Ala Pro Ala Ser Ser Ala Asn Met Ser Val Gly
1               5                   10                  15

Phe Asp Val Leu Gly Ala Ala Val Thr Pro Val Asp Gly Ala Leu Leu
            20                  25                  30

Gly Asp Val Val Thr Val Glu Ala Ala Glu Thr Phe Ser Leu Asn Asn
        35                  40                  45

Leu Gly Arg Phe Ala Asp Lys Leu Pro Ser Glu Pro Arg Glu Asn Ile
    50                  55                  60

Val Tyr Gln Cys Trp Glu Arg Phe Cys Gln Glu Leu Gly Lys Gln Ile
65                  70                  75                  80

Pro Val Ala Met Thr Leu Glu Lys Asn Met Pro Ile Gly Ser Gly Leu
                85                  90                  95

Gly Ser Ser Ala Cys Ser Val Val Ala Ala Leu Met Ala Met Asn Glu
            100                 105                 110

His Cys Gly Lys Pro Leu Asn Asp Thr Arg Leu Leu Ala Leu Met Gly
        115                 120                 125

Glu Leu Glu Gly Arg Ile Ser Gly Ser Ile His Tyr Asp Asn Val Ala
    130                 135                 140

Pro Cys Phe Leu Gly Gly Met Gln Leu Met Ile Glu Glu Asn Asp Ile
145                 150                 155                 160

Ile Ser Gln Gln Val Pro Gly Phe Asp Glu Trp Leu Trp Val Leu Ala
                165                 170                 175

Tyr Pro Gly Ile Lys Val Ser Thr Ala Glu Ala Arg Ala Ile Leu Pro
            180                 185                 190

Ala Gln Tyr Arg Arg Gln Asp Cys Ile Ala His Gly Arg His Leu Ala
        195                 200                 205

Gly Phe Ile His Ala Cys Tyr Ser Arg Gln Pro Glu Leu Ala Ala Lys
    210                 215                 220

Leu Met Lys Asp Val Ile Ala Glu Pro Tyr Arg Glu Arg Leu Leu Pro
225                 230                 235                 240

Gly Phe Arg Gln Ala Arg Gln Ala Val Ala Glu Ile Gly Ala Val Ala
                245                 250                 255

Ser Gly Ile Ser Gly Ser Gly Pro Thr Leu Phe Ala Leu Cys Asp Lys
            260                 265                 270

Pro Glu Thr Ala Gln Arg Val Ala Asp Trp Leu Gly Lys Asn Tyr Leu
        275                 280                 285

Gln Asn Gln Glu Gly Phe Val His Ile Cys Arg Leu Asp Thr Ala Gly
    290                 295                 300

Ala Arg Val Leu Glu Asn
305                 310
```

<210> SEQ ID NO 6
<211> LENGTH: 933
<212> TYPE: DNA

<213> ORGANISM: Escherichia coli

<400> SEQUENCE: 6

```
atggttaaag tttatgcccc ggcttccagt gccaatatga gcgtcgggtt tgatgtgctc      60
ggggcggcgg tgacacctgt tgatggtgca ttgctcggag atgtagtcac ggttgaggcg     120
gcagagacat tcagtctcaa caacctcgga cgctttgccg ataagctgcc gtcagaacca     180
cgggaaaata tcgtttatca gtgctgggag cgttttttgcc aggaactggg taagcaaatt    240
ccagtggcga tgaccctgga aaagaatatg ccgatcggtt cgggcttagg ctccagtgcc    300
tgttcggtgg tcgcggcgct gatggcgatg aatgaacact gcggcaagcc gcttaatgac    360
actcgtttgc tggctttgat gggcgagctg gaaggccgta tctccggcag cattcattac    420
gacaacgtgg caccgtgttt tctcggtggt atgcagttga tgatcgaaga aaacgacatc    480
atcagccagc aagtgccagg gtttgatgag tggctgtggg tgctggcgta tccggggatt    540
aaagtctcga cggcagaagc cagggctatt ttaccggcgc agtatcgccg ccaggattgc    600
attgcgcacg gcgacatct ggcaggcttc attcacgcct gctattccg tcagcctgag     660
cttgccgcga agctgatgaa agatgttatc gctgaaccct accgtgaacg gttactgcca    720
ggcttccggc aggcgcggca ggcggtcgcg gaaatcggcg cggtagcgag cggtatctcc    780
ggctccggcc cgaccttgtt cgctctgtgt gacaagccgg aaaccgccca gcgcgttgcc    840
gactggttgg gtaagaacta cctgcaaaat caggaaggtt ttgttcatat ttgccggctg    900
gatacggcgg gcgcacgagt actggaaaac taa                                  933
```

<210> SEQ ID NO 7
<211> LENGTH: 309
<212> TYPE: PRT
<213> ORGANISM: Artificial Sequence
<220> FEATURE:
<223> OTHER INFORMATION: Modified metA

<400> SEQUENCE: 7

```
Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175
```

Ala Leu Leu Thr Arg Gly Phe Asp Asp Ser Phe Leu Ala Pro His Ser
              180                 185                 190

Arg Tyr Ala Asp Phe Pro Ala Ala Leu Ile Arg Asp Tyr Thr Asp Leu
         195                 200                 205

Glu Ile Leu Ala Glu Thr Glu Glu Gly Asp Ala Tyr Leu Phe Ala Ser
     210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                 245                 250                 255

Pro Asp Val Pro Tyr Asn Tyr Phe Pro His Asn Asp Pro Gln Asn Thr
             260                 265                 270

Pro Arg Ala Ser Trp Arg Ser His Gly Asn Leu Leu Phe Thr Asn Trp
         275                 280                 285

Leu Asn Tyr Tyr Val Tyr Gln Ile Thr Pro Tyr Asp Leu Arg His Met
     290                 295                 300

Asn Pro Thr Leu Asp
305

<210> SEQ ID NO 8
<211> LENGTH: 933
<212> TYPE: DNA
<213> ORGANISM: Artificial Sequence
<220> FEATURE:
<223> OTHER INFORMATION: Modified metA

<400> SEQUENCE: 8

```
atggttaaag tttatgcccc ggcttccagt gccaatatga gcgtcgggtt tgatgtgctc      60
ggggcggcgg tgacacctgt tgatggtgca ttgctcggag atgtagtcac ggttgaggcg     120
gcagagacat tcagtctcaa caacctcgga cgctttgccg ataagctgcc gtcagaacca     180
cgggaaaata tcgtttatca gtgctgggag cgttttttgcc aggaactggg taagcaaatt     240
ccagtggcga tgaccctgga aaagaatatg ccgatcggtt cgggcttagg ctccagtgcc     300
tgttcggtgg tcgcggcgct gatggcgatg aatgaacact gcggcaagcc gcttaatgac     360
actcgttttgc tggctttgat gggcgagctg gaaggccgta tctccggcag cattcattac     420
gacaacgtgg caccgtgttt tctcggtggt atgcagttga tgatcgaaga aaacgacatc     480
atcagccagc aagtgccagg gtttgatgag tggctgtggg tgctggcgta tccggggatt     540
aaagtctcga cggcagaagc cagggctatt taccggcgc agtatcgccg ccaggattgc     600
attgcgcacg gcgacatct ggcaggcttc attcacgcct gctattcccg tcagcctgag     660
cttgccgcga gctgatgaa agatgttatc gctgaaccct accgtgaacg gttactgcca     720
ggcttccggc aggcgcggca ggcggtcgcg gaaatcggcg cggtagcgag cggtatctcc     780
ggctccggcc cgaccttgtt cgctctgtgt gacaagccgg aaaccgccca gcgcgttgcc     840
gactggttgg gtaagaacta cctgcaaaat caggaaggtt tgttcatat ttgccggctg     900
gatacggcgg gcgcacgagt actggaaaac taa                                  933
```

<210> SEQ ID NO 9
<211> LENGTH: 22
<212> TYPE: DNA
<213> ORGANISM: Artificial Sequence
<220> FEATURE:
<223> OTHER INFORMATION: yjeH primer

<400> SEQUENCE: 9
aagctttgat aactctcctt tg                                              22

<210> SEQ ID NO 10
<211> LENGTH: 22
<212> TYPE: DNA
<213> ORGANISM: Artificial Sequence
<220> FEATURE:
<223> OTHER INFORMATION: yjeH primer

<400> SEQUENCE: 10
aagctttatg tggttatgcc at                                              22

<210> SEQ ID NO 11
<211> LENGTH: 28
<212> TYPE: DNA
<213> ORGANISM: Artificial Sequence
<220> FEATURE:
<223> OTHER INFORMATION: yjeH gene primer

<400> SEQUENCE: 11
ggtaccaggt cgactctaga ggatcccc                                        28

<210> SEQ ID NO 12
<211> LENGTH: 23
<212> TYPE: DNA
<213> ORGANISM: Artificial Sequence
<220> FEATURE:
<223> OTHER INFORMATION: yjeH gene primer

<400> SEQUENCE: 12
ggtaccttat gtggttatgc cat                                             23

<210> SEQ ID NO 13
<211> LENGTH: 70
<212> TYPE: DNA
<213> ORGANISM: Artificial Sequence
<220> FEATURE:
<223> OTHER INFORMATION: MetB primer

<400> SEQUENCE: 13
ttaccccttg tttgcagccc ggaagccatt ttccaggtcg gcaattaaat catatgaata    60
tcctccttag                                                            70

<210> SEQ ID NO 14
<211> LENGTH: 70
<212> TYPE: DNA
<213> ORGANISM: Artificial Sequence
<220> FEATURE:
<223> OTHER INFORMATION: metB primer

<400> SEQUENCE: 14
ttactctggt gcctgacatt tcaccgacaa agcccaggga acttcatcac gtgtaggctg    60
gagctgcttc                                                            70

<210> SEQ ID NO 15
<211> LENGTH: 70
<212> TYPE: DNA
<213> ORGANISM: Artificial Sequence
<220> FEATURE:
<223> OTHER INFORMATION: thrB primer

<400> SEQUENCE: 15
aaagaatatg ccgatcggtt cgggcttagg ctccagtgcc tgttcggtgg gtgtaggctg    60
gagctgcttc                                                            70

<210> SEQ ID NO 16
<211> LENGTH: 70
<212> TYPE: DNA
<213> ORGANISM: Artificial Sequence
<220> FEATURE:
<223> OTHER INFORMATION: thrB primer

<400> SEQUENCE: 16
agacaaccga catcgctttc aacattggcg accggagccg ggaaggcaaa catatgaata     60
tcctccttag                                                            70

<210> SEQ ID NO 17
<211> LENGTH: 29
<212> TYPE: DNA
<213> ORGANISM: Artificial Sequence
<220> FEATURE:
<223> OTHER INFORMATION: metA primer

<400> SEQUENCE: 17
aattgatatc atgccgattc gtgtgccgg                                       29

<210> SEQ ID NO 18
<211> LENGTH: 34
<212> TYPE: DNA
<213> ORGANISM: Artificial Sequence
<220> FEATURE:
<223> OTHER INFORMATION: metA primer

<400> SEQUENCE: 18
aattaagctt ttaatccagc gttggattca tgtg                                 34

<210> SEQ ID NO 19
<211> LENGTH: 44
<212> TYPE: DNA
<213> ORGANISM: Artificial Sequence
<220> FEATURE:
<223> OTHER INFORMATION: metA G111E mutagenesis primer

<400> SEQUENCE: 19
ttgtaactgg tgcgccgctg gaactggtgg ggtttaatga tgtc                      44

<210> SEQ ID NO 20
<211> LENGTH: 44
<212> TYPE: DNA
<213> ORGANISM: Artificial Sequence
<220> FEATURE:
<223> OTHER INFORMATION: metA G111E mutagenesis primer

<400> SEQUENCE: 20
gacatcatta aaccccacca gttccagcgg cgcaccagtt acaa                      44

<210> SEQ ID NO 21
<211> LENGTH: 44
<212> TYPE: DNA
<213> ORGANISM: Artificial Sequence
<220> FEATURE:
<223> OTHER INFORMATION: metA EH mutagenesis primer

<400> SEQUENCE: 21
tgtaactggt gcgccgctgg aacatgtggg gtttaatgat gtcg                      44

<210> SEQ ID NO 22
<211> LENGTH: 44
<212> TYPE: DNA

<213> ORGANISM: Artificial Sequence
<220> FEATURE:
<223> OTHER INFORMATION: metA EH mutagenesis primer

<400> SEQUENCE: 22
cgacatcatt aaaccccaca tgttccagcg gcgcaccagt taca         44

<210> SEQ ID NO 23
<211> LENGTH: 29
<212> TYPE: DNA
<213> ORGANISM: Artificial Sequence
<220> FEATURE:
<223> OTHER INFORMATION: metA EH primer

<400> SEQUENCE: 23
aattgatatc atgccgattc gtgtgccgg         29

<210> SEQ ID NO 24
<211> LENGTH: 27
<212> TYPE: DNA
<213> ORGANISM: Artificial Sequence
<220> FEATURE:
<223> OTHER INFORMATION: metA EH primer

<400> SEQUENCE: 24
aattaagcct gctgaggtac gtttcgg         27

<210> SEQ ID NO 25
<211> LENGTH: 23
<212> TYPE: DNA
<213> ORGANISM: Artificial Sequence
<220> FEATURE:
<223> OTHER INFORMATION: metA WT primer

<400> SEQUENCE: 25
cagcaggtga ataaatttta ttc         23

<210> SEQ ID NO 26
<211> LENGTH: 20
<212> TYPE: DNA
<213> ORGANISM: Artificial Sequence
<220> FEATURE:
<223> OTHER INFORMATION: metA WT primer

<400> SEQUENCE: 26
cgcgaatgga agctgtttcc         20

<210> SEQ ID NO 27
<211> LENGTH: 42
<212> TYPE: DNA
<213> ORGANISM: Artificial Sequence
<220> FEATURE:
<223> OTHER INFORMATION: pKD3 primer

<400> SEQUENCE: 27
tttccgaaac gtacctcagc aggtgtaggc tggagctgct tc         42

<210> SEQ ID NO 28
<211> LENGTH: 43
<212> TYPE: DNA
<213> ORGANISM: Artificial Sequence
<220> FEATURE:
<223> OTHER INFORMATION: pKD3 primer

<400> SEQUENCE: 28
gaataaaatt tattcacctg ctgcatatga atatcctcct tag         43

<210> SEQ ID NO 29
<211> LENGTH: 31
<212> TYPE: DNA
<213> ORGANISM: Artificial Sequence
<220> FEATURE:
<223> OTHER INFORMATION: ppc 2 copy primer

<400> SEQUENCE: 29
gccggaattc tgtcggatgc gatacttgcg c                           31

<210> SEQ ID NO 30
<211> LENGTH: 30
<212> TYPE: DNA
<213> ORGANISM: Artificial Sequence
<220> FEATURE:
<223> OTHER INFORMATION: ppc 2 copy primer

<400> SEQUENCE: 30
gaaggagctc agaaaaccct cgcgcaaaag                             30

<210> SEQ ID NO 31
<211> LENGTH: 31
<212> TYPE: DNA
<213> ORGANISM: Artificial Sequence
<220> FEATURE:
<223> OTHER INFORMATION: ppc 2 copy primer

<400> SEQUENCE: 31
gccggagctc tgtcggatgc gatacttgcg c                           31

<210> SEQ ID NO 32
<211> LENGTH: 30
<212> TYPE: DNA
<213> ORGANISM: Artificial Sequence
<220> FEATURE:
<223> OTHER INFORMATION: ppc 2 copy primer

<400> SEQUENCE: 32
gaagggtacc agaaaaccct cgcgcaaaag                             30

<210> SEQ ID NO 33
<211> LENGTH: 30
<212> TYPE: DNA
<213> ORGANISM: Artificial Sequence
<220> FEATURE:
<223> OTHER INFORMATION: aspC 2 copy primer

<400> SEQUENCE: 33
tccgagctca taagcgtagc gcatcaggca                             30

<210> SEQ ID NO 34
<211> LENGTH: 30
<212> TYPE: DNA
<213> ORGANISM: Artificial Sequence
<220> FEATURE:
<223> OTHER INFORMATION: aspC 2 copy primer

<400> SEQUENCE: 34
tccgagctcg tccacctatg ttgactacat                             30

<210> SEQ ID NO 35
<211> LENGTH: 27
<212> TYPE: DNA
<213> ORGANISM: Artificial Sequence
<220> FEATURE:

```
<223> OTHER INFORMATION: asd 2 copy primer

<400> SEQUENCE: 35
ccggaattcc caggagagca ataagca                                      27

<210> SEQ ID NO 36
<211> LENGTH: 28
<212> TYPE: DNA
<213> ORGANISM: Artificial Sequence
<220> FEATURE:
<223> OTHER INFORMATION: asd 2 copy primer

<400> SEQUENCE: 36
ctagtctaga tgctctattt aactcccg                                     28

<210> SEQ ID NO 37
<211> LENGTH: 28
<212> TYPE: DNA
<213> ORGANISM: Artificial Sequence
<220> FEATURE:
<223> OTHER INFORMATION: asd 2 copy primer

<400> SEQUENCE: 37
ctagtctaga ccaggagagc aataagca                                     28

<210> SEQ ID NO 38
<211> LENGTH: 27
<212> TYPE: DNA
<213> ORGANISM: Artificial Sequence
<220> FEATURE:
<223> OTHER INFORMATION: asd 2 copy primer

<400> SEQUENCE: 38
ccggaattct gctctattta actcccg                                      27

<210> SEQ ID NO 39
<211> LENGTH: 23
<212> TYPE: DNA
<213> ORGANISM: Artificial Sequence
<220> FEATURE:
<223> OTHER INFORMATION: icd promoter primer

<400> SEQUENCE: 39
cccggggtat tttcagagat tat                                          23

<210> SEQ ID NO 40
<211> LENGTH: 30
<212> TYPE: DNA
<213> ORGANISM: Artificial Sequence
<220> FEATURE:
<223> OTHER INFORMATION: icd promoter primer

<400> SEQUENCE: 40
cccgggatcc tccttcgagc gctactggtt                                   30

<210> SEQ ID NO 41
<211> LENGTH: 32
<212> TYPE: DNA
<213> ORGANISM: Artificial Sequence
<220> FEATURE:
<223> OTHER INFORMATION: pro promoter primer

<400> SEQUENCE: 41
cccggggatc ctctgtgtgg aattctcgga ca                                32
```

```
<210> SEQ ID NO 42
<211> LENGTH: 30
<212> TYPE: DNA
<213> ORGANISM: Artificial Sequence
<220> FEATURE:
<223> OTHER INFORMATION: pro promoter primer

<400> SEQUENCE: 42
cccgggaatt cattaaagag gagaaaggat                                    30

<210> SEQ ID NO 43
<211> LENGTH: 29
<212> TYPE: DNA
<213> ORGANISM: Artificial Sequence
<220> FEATURE:
<223> OTHER INFORMATION: cysk promoter primer

<400> SEQUENCE: 43
cccgggagct tccagcctgt ttacgatga                                     29

<210> SEQ ID NO 44
<211> LENGTH: 29
<212> TYPE: DNA
<213> ORGANISM: Artificial Sequence
<220> FEATURE:
<223> OTHER INFORMATION: cysk promoter primer

<400> SEQUENCE: 44
cccgggtccc aatttcatac agttaagga                                     29

<210> SEQ ID NO 45
<211> LENGTH: 44
<212> TYPE: DNA
<213> ORGANISM: Artificial Sequence
<220> FEATURE:
<223> OTHER INFORMATION: icd promoter primer

<400> SEQUENCE: 45 gaaaagaaa aaaaattctg gcgattgtgt aggctggagc tgct                     44

<210> SEQ ID NO 46
<211> LENGTH: 48
<212> TYPE: DNA
<213> ORGANISM: Artificial Sequence
<220> FEATURE:
<223> OTHER INFORMATION: icd promoter primer

<400> SEQUENCE: 46
cggcaattca taatctctga aaatacgcca tggtccatat gaatatcc                48

<210> SEQ ID NO 47
<211> LENGTH: 44
<212> TYPE: DNA
<213> ORGANISM: Artificial Sequence
<220> FEATURE:
<223> OTHER INFORMATION: cysk promoter primer

<400> SEQUENCE: 47 gaaaagaaa aaaaattctg gcgattgtgt aggctggagc tgct                     44

<210> SEQ ID NO 48
<211> LENGTH: 44
<212> TYPE: DNA
<213> ORGANISM: Artificial Sequence
<220> FEATURE:
<223> OTHER INFORMATION: cysk promoter primer
```

<400> SEQUENCE: 48
gcgggatcat cgtaaacagg ctgccatggt ccatatgaat atcc          44

<210> SEQ ID NO 49
<211> LENGTH: 44
<212> TYPE: DNA
<213> ORGANISM: Artificial Sequence
<220> FEATURE:
<223> OTHER INFORMATION: pro promoter primer

<400> SEQUENCE: 49
gaaaaagaaa aaaaattctg gcgattgtgt aggctggagc tgct          44

<210> SEQ ID NO 50
<211> LENGTH: 48
<212> TYPE: DNA
<213> ORGANISM: Artificial Sequence
<220> FEATURE:
<223> OTHER INFORMATION: pro promoter primer

<400> SEQUENCE: 50
tgtccgagaa ttccacacag aggatcgcca tggtccatat gaatatcc      48

<210> SEQ ID NO 51
<211> LENGTH: 197
<212> TYPE: DNA
<213> ORGANISM: Artificial Sequence
<220> FEATURE:
<223> OTHER INFORMATION: icd promoter

<400> SEQUENCE: 51
gtattttcag agattatgaa ttgccgcatt atagcctaat aacgcgcatc tttcatgacg     60
gcaaacaata gggtagtatt gacaagccaa ttacaaatca ttaacaaaaa attgctctaa   120
agcatccgta tcgcaggacg caaacgcata tgcaacgtgg tggcagacga gcaaaccagt   180
agcgctcgaa ggaggat                                                  197

<210> SEQ ID NO 52
<211> LENGTH: 197
<212> TYPE: DNA
<213> ORGANISM: Artificial Sequence
<220> FEATURE:
<223> OTHER INFORMATION: pro promoter

<400> SEQUENCE: 52
gtattttcag agattatgaa ttgccgcatt atagcctaat aacgcgcatc tttcatgacg     60
gcaaacaata gggtagtatt gacaagccaa ttacaaatca ttaacaaaaa attgctctaa   120
agcatccgta tcgcaggacg caaacgcata tgcaacgtgg tggcagacga gcaaaccagt   180
agcgctcgaa ggaggat                                                  197

<210> SEQ ID NO 53
<211> LENGTH: 299
<212> TYPE: DNA
<213> ORGANISM: Artificial Sequence
<220> FEATURE:
<223> OTHER INFORMATION: cysk promoter

<400> SEQUENCE: 53
agcttccagc ctgtttacga tgatcccgct gcttaatctg ttcatcatgc ccgttgccgt     60
ttgtggcgcg acggcgatgt gggtcgattg ctatcgcgat aaacacgcga gtgtggcggta   120 acaatctacc ggttatttg taaaccgttt gtgtgaaaca ggggtggctt atgccgcccc    180

```
ttattccatc ttgcatgtca ttatttccct tctgtatata gatatgctaa atccttactt      240
ccgcatattc tctgagcggg tatgctacct gttgtatccc aatttcatac agttaagga      299
```

MICROORGANISM PRODUCING O-ACETYL-HOMOSERINE AND METHOD FOR PRODUCING O-ACETYLHOMOSERINE USING THE SAME

CROSS-REFERENCES TO RELATED APPLICATIONS

This application is a U.S. national phase application of International PCT Patent Application No. PCT/KR2015/005659, which was filed on Jun. 5, 2015, which claims priority to Korean Patent Application Nos. 10-2014-0068613, filed Jun. 5, 2014. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_053_00US_ST25.txt. The text file is 29 KB, was created on Dec. 5, 2016, and is being submitted electronically via EFS-Web.

TECHNICAL FIELD

The present disclosure relates to a microorganism producing O-acetylhomoserine in high yield and a method for producing O-acetylhomoserine using the microorganism.

BACKGROUND ART

O-acetylhomoserine acts as a precursor of methionine, which is a kind of essential amino acid in the body. Methionine is used not only as an additive for feeds and foods but also as a raw material for infusion solutions and pharmaceutical drugs.

Methionine is produced by chemical and biological syntheses. Recently, a two-step process for producing L-methionine from an L-methionine precursor, which was produced via fermentation, by enzymatic conversion was published (International Publication No. WO 2008/013432).

The two-step process employs O-succinylhomoserine and O-acetylhomoserine as precursors, and it is very important to produce O-acetylhomoserine in high yield for the purpose of economical mass production.

DISCLOSURE

Technical Problem

Under the circumstances, the present inventors have made efforts to improve the production of O-acetylhomoserine, and as a result, they have discovered a protein capable of exporting O-acetylhomoserine, thereby completing the present disclosure.

Technical Solution

An object of the present disclosure is to provide a microorganism having enhanced O-acetylhomoserine productivity.

Another object of the present disclosure is to provide a method for efficient production of O-acetylhomoserine using the microorganism having enhanced O-acetylhomoserine productivity.

Advantageous Effects of the Invention

The microorganism of the present disclosure with an enhanced activity of YjeH, i.e., an inner membrane protein, has an improved ability of exporting O-acetylhomoserine and thus the efficiency of O-acetylhomoserine production can be increased. Therefore, the microorganism of the present disclosure can be widely used for the production of O-acetylhomoserine.

DESCRIPTION OF DRAWINGS

FIG. 1 shows a cleavage map of the yjeH vector (pBAC-yjeH vector) according to the present disclosure.

BEST MODE

An aspect of the present disclosure provides a microorganism having O-acetylhomoserine productivity, in which the activity of YjeH, i.e., an inner membrane protein, is enhanced compared to a non-modified microorganism.

As used herein, the term "O-acetylhomoserine" refers to an acetyl derivative of L-homoserine, which is a specific intermediate material in the biosynthetic pathway of methionine in microorganisms. O-Acetylhomoserine is known to be produced by a reaction between homoserine and acetyl-CoA catalyzed by homoserine acetyltransferase. It has a chemical formula of $C_6H_{11}NO_4$.

As used herein, the term "a microorganism having O-acetylhomoserine productivity" refers to a microorganism which, when cultured in a culture medium, can produce O-acetylhomoserine within a bioorganism and secrete it into the culture medium. The O-acetylhomoserine productivity may be provided or enhanced by improvement of species. Specifically, the microorganism having O-acetylhomoserine productivity may be a microorganism of the genus *Escherichia* having O-acetylhomoserine productivity, and more specifically, *E. coli*. For example, the microorganism may be *E. coli* having lysine, threonine, isoleucine, or methionine productivity, but is not limited thereto. As used herein, the term "YjeH" is known as a protein which, being a member of the Amino Acid-Polyamine-Organocation (APC) family for amino acid transporters, is present in an inner membrane. YjeH is expected to act as an amino acid transporter but its exact function is not known yet. As such, the present inventors have confirmed first that YjeH specifically exports O-acetylhomoserine.

Specifically, YjeH may be derived from a microorganism of the genus *Escherichia*, and more specifically, from *E. coli*. In particular, YjeH may be a protein having an amino acid sequence of SEQ ID NO: 1, or any amino acid sequence having a homology of 70% or higher, specifically 80% or higher, or more specifically 90% or higher, to the amino acid sequence of SEQ ID NO: 1. Additionally, it is obvious that any amino acid sequence which has the same amino acid sequence as that of SEQ ID NO: 1, or any amino acid sequence having the activity of exporting O-acetylhomoserine, can belong to the scope of the present disclosure, although the sequence may have a partial deletion, modification, substitution, or addition therein. Additionally, based on genetic codon degeneracy, nucleotide sequences encoding the same amino acid and variants thereof belong to the scope of the present disclosure, for example, a nucleotide sequence represented by SEQ ID NO: 2, but are not limited thereto.

As used herein, the term "homology" refers to a degree of identity between two different sequences of nucleotides or amino acid residues in a particular comparison region of the nucleotide or amino acid sequences of a gene encoding a protein, after aligning both sequences to a maximal match. When the homology is sufficiently high, the expression products of the corresponding gene may have the same or similar activity. The homology may be determined using a sequence comparison program known in the art, e.g., BLAST (NCBI), CLC Main Workbench (CLC bio), MegAlign™ (DNASTAR Inc.), etc.

As used herein, the term "a non-modified microorganism" refers to a microorganism which is not introduced with a modification in the activity of the corresponding protein, and the microorganism refers to a base strain to be introduced with the modification in the activity of the corresponding protein, which may be a native or modified microorganism.

As used herein, the term "enhancement" of a protein activity refers to improving the activity state of proteins possessed by a microorganism. The enhancement of a protein activity is not limited as long as the activity of each protein can be enhanced compared to that of a non-modified microorganism, as is the case with the enhancement of the activity of a target protein. For example, the enhancement may be performed by methods selected from the group consisting of i) increasing the copy number of a polynucleotide encoding each protein, ii) modifying the expression control sequence for increasing the expression of the polynucleotide, iii) modifying the polynucleotide sequence on the chromosome for enhancing the activity of each protein; and iv) a combination thereof. Specifically, the enhancement of a protein activity may be performed by a method selected from the group consisting of a method of introducing a nucleotide sequence encoding each protein into the chromosome, a method of introducing the nucleotide sequence into a microorganism after introducing it into a vector system, a method of introducing a promoter exhibiting an improved activity into the upstream of the nucleotide sequence encoding each protein or introducing each protein with a modification on the promoter, a method of modifying the nucleotide sequence of the 5'-UTR region, and a method of introducing a variant of the nucleotide sequence encoding each protein, but the method is not limited thereto.

In a specific embodiment of the present disclosure, the YjeH activity may be enhanced compared to that of a non-modified microorganism, by increasing the copy number or enhancing the activity of a given promoter. Specifically, the YjeH activity may be enhanced by introducing a promoter exhibiting an improved activity to YjeH, which is an inner membrane. In a specific embodiment of the present disclosure, the promoter with an improved activity may include without limitation any promoter having an improved activity compared to that of the self-promoter of yjeH. Examples of such promoter may include without limitation any promoter of a gene having a higher activity of gene expression compared to that of the self-promoter of yjeH, or a modified promoter with an improved activity due to modification of the gene in the self-promoter of yjeH, etc. Specifically, the promoter of the present disclosure exhibiting an improved activity may be selected from the group consisting of icd promoter, pro promoter, and cysk promoter. Specifically, the icd promoter may consist of the nucleotide sequence of SEQ ID NO: 51; the pro promoter may consist of the nucleotide sequence of SEQ ID NO: 52; and the cysk promoter may consist of the nucleotide sequence of SEQ ID NO: 53, but each of the promoters may consist of a nucleotide sequence having a homology of 70% or higher, specifically 80% or higher, and more specifically 90% or higher, to each of the above nucleotide sequences.

In a specific aspect of the present disclosure, the microorganism of the genus *Escherichia* having O-acetylhomoserine productivity may be one in which the activity of cystathionine synthase is further weakened or inactivated. Specifically, the microorganism may be one in which the activity of cystathionine synthase is weakened or inactivated compared to that of a non-modified microorganism, and specifically the gene, metB which encodes cystathionine synthase, is deleted, but is not limited thereto. The amino acid sequence of metB may be obtained from a known database, and any amino acid sequence having the activity of cystathionine synthase may be included without limitation, for example, it may refer to a protein having the amino acid sequence of SEQ ID NO: 3. The protein having the amino acid sequence of SEQ ID NO: 3 may be a protein encoded by the nucleotide sequence of SEQ ID NO: 4, but is not limited thereto. Additionally, in another aspect of the present disclosure, the microorganism of the genus *Escherichia* may be one in which the activity of homoserine kinase is further weakened or inactivated. Specifically, the microorganism may be one in which the activity of homoserine kinase is weakened or inactivated compared to the endogenous activity of a non-modified microorganism, and specifically one in which the gene, thrB which encodes homoserine kinase, is deleted, but is not limited thereto. The amino acid sequence of thrB may be obtained from a known database, and any amino acid sequence having the activity of homoserine kinase may be included without limitation, for example, it may refer to a protein having the amino acid sequence of SEQ ID NO: 5. The protein having the amino acid sequence of SEQ ID NO: 5 may be a protein encoded by the nucleotide sequence of SEQ ID NO: 6, but is not limited thereto.

In the present disclosure, "weakening" of the activity of the protein may be performed by a method selected from the group consisting of i) deleting a part or entirety of the gene encoding each protein, ii) modifying the expression control sequence for decreasing the expression of the gene, iii) modifying the gene sequence on the chromosome for weakening the activity of the protein; and iv) a combination thereof, but is not limited thereto.

Specifically, the term "weakening of a protein activity" refers to a decrease in the activity of an enzyme compared to the endogenous activity of the enzyme possessed by a microorganism in its natural or base strain state. The weakening is a concept including a case when there is a decrease in the activity of an enzyme in a microorganism compared to that originally possessed by the enzyme itself due to a modification of the enzyme-encoding gene, etc., a case when the level of overall enzyme activity in a cell is lower than that of the wild-type strain due to inhibition of expression or inhibition of translation of the enzyme-encoding gene, or a combined case thereof, but is not limited thereto.

The "inactivation" refers to a case when the enzyme-encoding gene in a microorganism is not expressed at all and a case when the gene is expressed but exhibits no activity, compared to that of the wild-type strain.

The inactivation of an enzyme may be achieved by applying various methods known in the art. Examples of the methods may include a method of substituting the enzyme-encoding gene on the chromosome with a gene mutated to reduce the activity of the enzyme, including the case when the enzyme activity is eliminated; a method of introducing a modification in the expression control sequence of the enzyme-encoding gene on the chromosome; a method of substituting the expression control sequence of the enzyme-encoding gene with a sequence having weak or no activity; a method of deleting the entirety or a part of the enzyme-encoding gene on the chromosome; a method of introducing an antisense oligonucleotide (e.g., antisense RNA) which binds complementary to a transcript of the gene on the chromosome, thereby inhibiting the translation from the mRNA into the enzyme; a method of artificially incorporating a complementary sequence to the SD sequence into the upstream of the SD sequence of the enzyme-encoding gene, forming a secondary structure, thereby making the attachment of ribosome thereto impossible; a method of incorporating a promoter to the 3' terminus of the open reading frame (ORF) of the corresponding sequence to induce a reverse transcription (reverse transcription engineering (RTE)), etc., and also a combination thereof, but are not limited thereto.

Specifically, the method of deleting the entirety or a part of a gene encoding an enzyme may be performed by substituting the polynucleotide encoding the endogenous target protein within the chromosome with a polynucleotide or marker gene having a partial deletion in the nucleic acid sequence using a vector for chromosomal insertion within a strain. In an exemplary embodiment of the method of deleting a part or the entirety of a gene, a method for deleting a gene by homologous recombination may be used, but is not limited thereto.

As used herein, the term "a part" may vary depending on the kinds of polynucleotides, and it may specifically refer to 1 to 300, more specifically 1 to 100, and even more specifically 1 to 50, but is not particularly limited thereto.

As used herein, the term "homologous recombination" refers to genetic recombination that occurs via crossover at a locus of a gene chain having a mutual homology.

Specifically, the expression regulatory sequence may be modified by inducing a modification of the expression control sequence by deletion, insertion, non-conservative or conservative substitution, or a combination thereof to further weaken the activity of the expression control sequence; or by substituting with a promoter having much weaker activity. The expression control sequence may include a promoter, an operator sequence, a sequence encoding a ribosome-binding region, and sequences controlling the termination of transcription and translation, but is not limited thereto.

Furthermore, the gene sequence on the chromosome may be modified by inducing a modification in the sequence by deletion, insertion, non-conservative or conservative substitution, or a combination thereof in the gene sequence for further weakening the enzyme activity; or by substituting with a gene sequence which was improved to have a weaker activity or a gene sequence which was improved to have no activity, but is not limited thereto.

In a specific embodiment of the present disclosure, the activity of each protein was weakened by deleting the metB gene encoding cystathionine synthase and/or the thrB gene by homologous recombination.

Additionally, in a specific embodiment of the present disclosure, the microorganism of the genus *Escherichia* may be one in which, additionally, the activity of homoserine acetyltransferase is enhanced compared to that of a non-modified microorganism. Specifically, the microorganism may be one in which the activity of homoserine acetyltransferase is increased compared to that of a non-modified microorganism, and in particular, the microorganism may be one in which a modified metA gene encoding homoserine acetyltransferase having an enhanced activity is introduced. The modified metA gene may be a gene encoding homoserine acetyltransferase, in which the 111th amino acid of homoserine acetyltransferase is substituted with glutamic acid and the $112^{th}$ amino acid is substituted with histidine, and in particular, a gene which consists of the nucleotide sequence of SEQ ID NO: 8, but is not limited thereto. The modified metA gene may include without limitation any amino acid in which the activity of homoserine acetyltransferase is enhanced compared to that of wild-type, e.g., a protein having the amino acid sequence of SEQ ID NO: 7. An exemplary embodiment with respect to the preparation, utilization of the modified metA gene, a strain with an enhanced activity of homoserine acetyltransferase, etc., is disclosed in Korean Patent No. 10-1335841, and the entirety of the Korean Patent may be included as a reference to the present disclosure.

Additionally, in a specific aspect of the present disclosure, the microorganism of the genus *Escherichia* may be one in which the activity of aspartate kinase (EC 2.7.2.4) is enhanced compared to that of a non-modified microorganism. Specifically, the microorganism may be one in which the activity of aspartate kinase is increased compared to that of the endogenous activity of the microorganism, but is not limited thereto.

In a specific embodiment of the present disclosure, the biosynthetic pathway was further enhanced for the purpose of maximizing the O-acetylhomoserine productivity. Specifically, aspartate kinase and homoserine O-acetyltransferase were introduced using a plasmid, and the change in O-acetylhomoserine productivity was measured after further enhancing YjeH in the strain with an enhanced biosynthetic pathway for homoserine. As a result of the simultaneous enhancement of both biosynthetic pathway and yjeH, it was confirmed that the O-acetylhomoserine productivity was further improved. In particular, it was confirmed that when the YjeH activity was enhanced using the cysk promoter, the YjeH productivity was increased by about 93% (2.8 g/L→5.4 g/L) (Table 5).

Additionally, in a specific embodiment of the present disclosure, it was examined whether the enhancement of YjeH activity in an existing strain having high-yield O-acetylhomoserine productivity can further increase its O-acetylhomoserine productivity. More specifically, the amount of O-acetylhomoserine production was examined using a strain KCCM11146P (International Publication No. WO2012/087039) producing O-acetylhomoserine prepared from the strain having threonine productivity by NTG mutation, which a wild-type W3110-derived strain after substituting the promoter of the endogenous yjeH gene with a promoter with high expression-inducing activity. As a result, it was confirmed that the strain, which already has high-yield O-acetylhomoserine productivity, can further increase the activity of producing O-acetylhomoserine by the enhancement of YjeH activity by about 14% (14.2 g/L→18.2 g/L), and in particular, by the enhancement of YjeH activity using the cysk promoter (Table 7).

Information on the genes used in the present disclosure, the sequences of the proteins encoded by the genes, and promoter sequences can be obtained from a known database, e.g., NCBI GenBank, but is not limited thereto.

The genes encoding each of the proteins and promoters of the present disclosure include not only the nucleotide sequences represented by each of the SEQ ID NOS. but also include without limitation any gene sequence having a homology of 80% or higher, specifically 90% or higher, more specifically 95% or higher, even more specifically 98% or higher, and most specifically 99% or higher, to these sequences, as long as the gene sequence encodes an enzyme which exhibits an effect substantially the same as or corresponding to that of each of the enzymes described above. Additionally, it is obvious that any nucleotide sequence having the above sequence homology must also belong to the scope of the present disclosure, although the amino acid may have deletion, modification, substitution, or addition in part of the sequence.

Additionally, it is obvious that any amino acid constituting each of the above proteins of the present disclosure must also belong to the scope of the present disclosure although the amino acid may have deletion, modification, substitution, or addition in part of the sequence, as long as the amino acid has the same sequence represented by each of the SEQ ID NOS. or has a homology thereto while having an effect substantially the same as or corresponding to that of each of the proteins.

The effect of uniformly increasing O-acetylhomoserine productivity by the enhancement of YjeH activity was confirmed based on microorganisms having various genetic backgrounds and O-acetylhomoserine productivities. This may occur by promoting the production of a specific intermediate material by YjeH in the biosynthetic pathway. However, considering the characteristics of YjeH, which is an inner membrane and a kind of amino acid transporter family, the increase of O-acetylhomoserine productivity is thought to be achieved by increasing the ability of exporting O-acetylhomoserine, which is a final product and a kind of amino acid, thereby promoting intracellular reactions.

In still another aspect of the present disclosure, the present disclosure provides a method for producing O-succinylhomoserine including culturing a microorganism of the genus *Escherichia* producing O-acetylhomoserine of the present disclosure and recovering the cultured medium.

The medium used for culturing the microorganism of the present disclosure and other culture conditions are not particularly limited but any medium used for the conventional culturing of the microorganism of the genus *Escherichia* may be used. Specifically, the microorganism of the present disclosure may be cultured in a conventional medium containing appropriate carbon sources, nitrogen sources, phosphorous sources, inorganic compounds, amino acids and/or vitamins, etc., in an aerobic condition while adjusting temperature, pH, etc.

In the present disclosure, the carbon sources may include carbohydrates (e.g., glucose, fructose, sucrose, maltose, mannitol, sorbitol, etc.); alcohols (e.g., sugar alcohol, glycerol, pyruvic acid, lactic acid, citric acid, etc.); amino acids (e.g., glutamic acid, methionine, lysine, etc.); etc., but are not limited thereto. Additionally, the carbon sources may include natural organic nutrients such as starch hydrolysate, molasses, blackstrap molasses, rice bran, cassava, sugar cane molasses, corn steep liquor, etc. Specifically, carbohydrates such as glucose and sterilized pretreated molasses (i.e., molasses converted to reducing sugar) may be used, and in addition, various other carbon sources in an appropriate amount may be used without limitation. These carbon sources may be used alone or in combination of at least two kinds.

Examples of the nitrogen sources may include inorganic nitrogen sources (e.g., ammonia, ammonium sulfate, ammonium chloride, ammonium carbonate, ammonium phosphate, ammonium nitrate, etc.); amino acids (glutamic acid, methionine, glutamine, etc.); and organic nitrogen sources (e.g., peptone, N-Z amine, meat extract, yeast extract, malt extract, corn steep liquor, casein hydrolysate, fish or decomposition product thereof, defatted soybean cake or decomposition product thereof, etc.). These nitrogen sources may be used alone or in combination of at least two kinds, but are not limited thereto.

Examples of the phosphorus sources may include monopotassium phosphate, dipotassium phosphate, and corresponding sodium-containing salts. Examples of inorganic compounds to be used may include sodium chloride, calcium chloride, iron chloride, magnesium sulfate, iron sulfate, manganese sulfate, calcium carbonate, etc. Additionally, amino acids, vitamins, and/or appropriate precursors may be included. These media or precursors may be added in a batch culture process or a continuous culture process to a culture, but are not limited thereto.

In the present disclosure, the pH of a culture may be adjusted during the cultivation by adding a compound such as ammonium hydroxide, potassium hydroxide, ammonia, phosphoric acid, and sulfuric acid to the culture in an appropriate manner. During the cultivation, an antifoaming agent, such as fatty acid polyglycol ester, may also be added to prevent foam generation. Additionally, oxygen or an oxygen-containing gas may be injected into the culture in order to maintain an aerobic state of the culture; or nitrogen, hydrogen, or carbon dioxide gas may be injected without the injection of a gas in order to maintain an anaerobic or microaerobic state of the culture.

The culture temperature may generally be in a range from 27° C. to 37° C., and more specifically, from 30° C. to 35° C., but is not limited thereto. The cultivation may be continued until the desired amount of useful materials is obtained, and specifically for from 10 hours to 100 hours, but is not limited thereto.

The method of producing O-acetylhomoserine of the present disclosure may further include a method of recovering O-acetylhomoserine from the cultured microorganism or the cultured medium.

Specifically, the recovering of O-acetylhomoserine may be performed by a method of culturing microorganisms of the present disclosure, for example, an appropriate method known in the art such as a batch process, a continuous batch process, or a fed-batch process.

The recovering may include a purification process.

The thus-recovered O-acetylhomoserine may be used to produce methionine by a two-step process developed by the present inventors (Korean Patent No. 10-0905381), i.e., a two-step process.

The two-step process includes a process for producing L-methionine and organic acids by an enzymatic reaction using an enzyme having the activity of O-acetylhomoserine sulfhydrylase or a strain containing the enzyme by utilizing O-acetylhomoserine produced by a strain producing the L-methionine precursor and methyl mercaptan as substrates.

More specifically, the present disclosure provides a method for producing L-methionine by an enzyme reaction using an enzyme such as O-acetylhomoserine sulfhydrylase by utilizing O-acetylhomoserine accumulated by the above method as a substrate.

In the two-step process, when O-acetylhomoserine is used as a precursor of L-methionine, specifically, O-acetylhomoserine sulfhydrylase derived from a microorganism strain belonging to the genus *Leptospira*, the genus *Chromobacterium*, and the genus *Hyphomonas*, and more specifically, from a microorganism strain belonging to *Leptospira meyeri, Pseudomonas aurogenosa, Hyphomonas neptunium*, and *Chromobacterium violaceum* may be used.

The reaction is shown below.

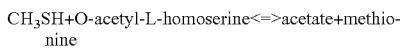
CH₃SH+O-acetyl-L-homoserine<=>acetate+methionine

Such additional methionine-producing process is disclosed in Korean Patent No. 10-0905381, and the entire specification of the above Korean patent may be included as a reference to the present disclosure.

MODE FOR INVENTION

Hereinafter, the present disclosure will be described in more detail with reference to the following Examples. However, these Examples are for illustrative purposes only, and the disclosure is not intended to be limited by these Examples.

Example 1: Preparation of Strains Having O-Acetylhomoserine Productivity 1-1. Deletion of metB Gene in Wild-Type *E. coli*

For the preparation of a strain producing O-acetylhomoserine, *E. coli*, a representative microorganism of the genus *Escherichia*, was used. To this end, a wild-type *E. coli* (K12) W3110 (ATCC27325) was obtained from the American Type Culture Collection (ATCC) and used. First, for blocking the pathway of producing cystathionine from O-succinyl-L-homoserine, the metB gene (SEQ ID NO: 4) encoding cystathionine synthase was deleted.

Specifically, an FRT one-step PCR deletion method was used for the deletion of metB gene (Wanner B L., *Proc. Natl. Acad. Sci. USA* 97: 6640-6645, 2000). A deletion cassette was prepared by performing PCR based on the pKD3 vector (Wanner B L., *Proc. Natl. Acad. Sci. USA* 97: 6640-6645, 2000) as a template using the primers TKd of SEQ ID NOS: 13 and 14. In particular, PCR was performed for a total of 30 cycles under the following conditions: denaturation at 94° C. for 30 sec, annealing at 55° C. for 30 sec, and extension at 72° C. for 1 min.

The thus-obtained PCR product was electrophoresed on a 1.0% agarose gel, and the DNA obtained from a 1.2 kb band was purified. The recovered DNA fragment was introduced into the *E. coli* (K12) W3110 strain, which was already transformed with the pKD46 vector (Wanner B L., *Proc. Natl. Acad. Sci. USA* 97: 6640-6645, 2000), by electroporation. The W3110 strain transformed with pKD46 was cultured using LB medium containing ampicillin (100 μg/L) and L-arabinose (5 mM) until the culture reached an $OD_{600}$=0.6 at 30° C., and used after washing twice with sterile distilled water and once with 10% glycerol. The electroporation was performed at 2500 V. The recovered strain was spread on LB plate medium containing chloramphenicol (25 μg/L), cultured overnight at 37° C., and the resistant strains were selected.

PCR was performed using the thus-selected strain as a template along with the same primers (SEQ ID NOS: 13 and 14), and the deletion of the metB gene was confirmed by observing the presence of a 1.2 kb gene band on a 1.0% agarose gel. The strain, in which the deletion of metB gene was confirmed, was transformed with pCP20 vector (Wanner B L., *Proc. Natl. Acad. Sci. USA* 97: 6640-6645, 2000) and cultured in the same LB medium. Then, PCR was performed under the same conditions followed by electrophoresis on a 1.0% agarose gel to observe the presence of a 1.2 kb gene band, thus confirming the deletion of metB gene. The strain, upon confirmation of the deletion, was transformed with pCP20 vector (Wanner B L., *Proc. Natl. Acad. Sci. USA* 97: 6640-6645, 2000) and cultured in the same LB medium. Then, PCR was performed under the same conditions followed by electrophoresis on a 1.0% agarose gel to select the final strain with the deletion of metB gene represented by the gene band, which was reduced to a size of 150 bp, thereby confirming the removal of the chloramphenicol marker from the strain.

The thus prepared and selected strain, with the deletion of metB gene, encoding cystathionine synthase was named as "W3-B".

1-2. Deletion of thrB Gene

For increasing the amount of O-succinylhomoserine synthesis from the W3-B strain prepared in Example 1-1, thrB gene (SEQ ID NO: 6) encoding homoserine kinase was deleted from the strain. For the deletion of thrB gene, the same FRT one-step PCR deletion method, which was used in the deletion of metB gene in Example 1-1, was used.

First, for the preparation of a thrB deletion cassette, PCR was performed using the pKD4 vector (Wanner B L., *Proc. Natl. Acad. Sci. USA* 97: 6640-6645, 2000) as a template and thereby a deletion cassette was prepared. Specifically, PCR was performed using the primers of SEQ ID NOS: 15 and 16 for a total of 30 cycles under the following conditions: denaturation at 94° C. for 30 sec, annealing at 55° C. for 30 sec, and extension at 72° C. for 1 min.

The thus-obtained PCR product was electrophoresed on a 1.0% agarose gel, and the DNA obtained from a 1.6 kb band was purified. The recovered DNA fragment was introduced into the W3-B strain, which was already transformed with the pKD46 vector by electroporation. The recovered strain was spread on LB plate medium containing kanamycin (50 μg/L), cultured overnight at 37° C., and the resistant strains were selected.

PCR was performed under the same conditions using the strain selected through the above process as a template along with primers (SEQ ID NOS: 15 and 16), and the deletion of the thrB gene was confirmed by observing the presence of a 1.6 kb gene on a 1.0% agarose gel. The strain confirmed was transformed again with the pCP20 vector and cultured on LB medium, and then, PCR was performed under the same conditions followed by electrophoresis on a 1.0% agarose gel to select the final strain with the deletion of thrB gene represented by the gene band, which was reduced to a size of 150 bp, thereby confirming the removal of the kanamycin marker from the strain. The thus-prepared and selected strain, with the deletion of thrB gene, encoding homoserine kinase was named as "W3-BT".

Exemplary embodiments with respect to the strains with the deletion of metB gene and thrB gene, etc., are disclosed in Korean Patent No. 10-0905381 or International Publication No. WO 2008/013432, and the entire specification of the Korean patent or the international patent publication may be included herein as a reference to the present disclosure.

1-3. Preparation of a Strain with Modified metA Gene Having an Activity of Homoserine Acetyltransferase For enhancing the activity of homoserine acetyltransferase in the strain prepared in Example 1-2, an attempt was made to introduce a modified metA gene (SEQ ID NO: 8), which encodes homoserine acetyltransferase with an enhanced activity, to the strain.

In this regard, for the preparation of a modified metA gene with an enhanced activity, the metA gene was first amplified and obtained by PCR using the chromosome of the W3110 strain as a template along with primers (SEQ ID NOS: 17 and 18). The primers (SEQ ID NOS: 17 and 18) used in the PCR were prepared to include an EcoRV restriction site and a HindIII restriction site, respectively, based on the nucleotide sequence of *E. coli* chromosome of NC_000913 registered in the NIH GenBank.

The thus-obtained PCR product and the pCL1920 plasmid including pcj1 were treated with EcoRV and HindIII and cloned. *E. coli* DH5α was transformed with the cloned plasmid and cultured in LB plate medium containing spectinomycin (50 μg/L), and the transformed *E. coli* DH5a was selected and thereby the plasmid was obtained. The thus-obtained plasmid was named as "pCL_Pcj1_metA".

A modified metA gene was prepared using the site-directed mutagenesis kit (Stratagene, USA) based on the pCL_Pcj1_metA obtained above. Specifically, the 111$^{th}$ amino acid (Gly) of homoserine acetyltransferase was substituted with glutamic acid (Glu) (G111E). The thus-prepared plasmid was named as "pCL_Pcj1_metA(EL)".

Additionally, the 111$^{th}$ amino acid (Gly) of homoserine acetyltransferase was substituted with glutamic acid (Glu), and additionally, the 112$^{th}$ amino acid (Leu) was substituted with histidine (His) using the primers (SEQ ID NOS: 21 and 22). Accordingly, the plasmid including the metA gene, in which the 111th amino acid was changed from glycine to glutamic acid and the 112$^{th}$ amino acid was changed from leucine to histidine, was named as "pCL_Pcj1_metA(EH)".

Then, for preparing a replacement cassette to substitute with the modified metA gene after introducing it into a strain, PCR was performed using the pKD3 vector as a template along with primers (SEQ ID NOS: 27 and 28) for a total of 30 cycles under the following conditions: denaturation at 94° C. for 30 sec, annealing at 55° C. for 30 sec, and extension at 72° C. for 2 min. The metA(EH) part of the replacement cassette was obtained as a PCR product using pCL-Pcj1-metA(EH) as a template along with primers (SEQ ID NOS: 23 and 24) and the part of the metA wild-type was obtained using primers (SEQ ID NOS: 25 and 26), respectively. The three PCR products were used for the preparation of the metA(EH) replacement cassette, which includes a chloramphenicol marker, using primers (SEQ ID NOS: 23 and 26), and the modified metA gene was introduced into the W3-BT strain, which was already transformed with pKD46 vector, prepared in Example 1-2 by electroporation. The strain, in which the introduction was confirmed, was again transformed with pCP20 vector, cultured in LB medium, and the strain in which the chloramphenicol marker was removed and the metA gene was substituted with metA(EH) was named as "W3-BTA".

Exemplary embodiments with respect to the strains with enhanced activity of homoserine acetyltransferase, etc., are disclosed in Korean Patent No. 10-1335841 or International Publication No. WO 2012/087039, and the entire specification of the Korean patent or the international patent publication may be included herein as a reference to the present disclosure.

1-4. Preparation of Strains Including 2 Copies of ppc, aspC, and asd Genes

For increasing the O-acetylhomoserine productivity of W3-BTA prepared in Example 1-3, the existing strategy for enhancing biosynthetic pathway was introduced. Efforts were made to prepare a strain, in which phosphoenolpyruvate carboxylase involved in the biosynthesis of oxaloacetate from phosphoenolpyruvate, aspartate aminotransferase involved in the biosynthesis of aspartate from oxaloacetate, and aspartate-semialdehyde dehydrogenase involved in the biosynthesis of homoserine from aspartate-semialdehyde dehydrogenase (i.e., ppc gene, aspC gene, and asd gene) were amplified into 2 copies.

Accordingly, ppc gene was amplified into 2 copies using the primers of SEQ ID NOS: 29, 30, 31, and 32; aspC gene was amplified into 2 copies using the primers of SEQ ID NOS: 33 and 34; and asd gene was amplified into 2 copies using the primers of SEQ ID NOS: 35, 36, 37, and 38, respectively.

The strain, in which the biosynthetic pathway for O-acetylhomoserine was enhanced based on W3-BTA strain by the above process, was named as "W3-BTA2PCD (=WCJM)".

Exemplary embodiments with respect to the strains with enhanced activity of homoserine acetyltransferase, etc., are disclosed in Korean Patent No. 10-0905381 or International Publication No. WO 2008/013432, and the entire specification of the Korean patent or the international patent publication may be included herein as a reference to the present disclosure.

1-5. Experiment of Flask Culture

For the experiment of the amount of O-acetylhomoserine production by the strains prepared in Examples 1-3 and 1-4, an Erlenmeyer flask culture was performed. The W3110, W3-BTA, and WCJM strains were inoculated into LB medium, cultured at 33° C. overnight. Then, a single colony was inoculated into LB medium (3 mL), cultured at 33° C. for 5 hours, again diluted 200-fold in a 250 mL Erlenmeyer flask containing 25 mL of medium for producing O-acetylhomoserine, cultured at 33° C. at a rate of 200 rpm for 30 hours, and the amount of O-acetylhomoserine production was confirmed by HPLC analysis. The medium composition used is summarized in Table 1 below.

TABLE 1

Composition for flask medium for producing O-acetylhomoserine

| Composition | Concentration (per Liter) |
|---|---|
| Glucose | 40 g |
| Ammonium sulfate | 17 g |
| $KH_2PO_4$ | 1.0 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| $ZnSO_4$ | 5 mg |
| Calcium carbonate | 30 g |
| Yeast extract | 2 g |
| Methionine | 0.15 g |
| Threonine | 0.15 g |

The strains were cultured in the above medium for 30 hours and the amounts of O-acetylhomoserine production were confirmed by HPLC analysis. The results are shown in Table 2 below.

TABLE 2

O-acetylhomoserine production by flask culture

| | OD (562 nm) | Glucose Consumption (g/L) | O-AH (g/L) |
|---|---|---|---|
| W3110 | 14.2 | 40 | 0 |
| W3-BTA | 8.4 | 36 | 0.9 |
| WCJM | 9.6 | 35 | 1.2 |

As can be confirmed from Table 2, wild-type W3110 strain did not produce O-acetylhomoserine at all, however, the W3-BTA strain produced O-acetylhomoserine in a concentration of 0.9 g/L, and the WCJM strain, in which the biosynthetic pathway is enhanced, produced O-acetylhomoserine in a concentration of 1.2 g/L.

Example 2: Identification of Membrane Proteins Increasing the O-Acetylhomoserine Productivity The present inventors have applied yjeH (SEQ ID NO: 1), of which the association with O-acetylhomoserine exportation and O-acetylhomoserine productivity has never been disclosed.

The yjeH gene of a strain was enhanced by cloning the yjeH gene into the bac vector using the HindIII restriction site present in the bac vector. For the bac vector, the CopyControl BAC Cloning kit (Cat. No. CCBAC1H-HindIII, Epicentre) was used.

First, for obtaining the yjeH gene, PCR was performed using primers (SEQ ID NOS: 9 and 10) for a total of 30 cycles under the following conditions: denaturation at 94° C. for 30 sec, annealing at 55° C. for 30 sec, and extension at 68° C. for 1 min. The resulting PCR product was electrophoresed on a 1.0% agarose gel, and the DNA obtained from a 1.2 kb band was purified. The purified DNA was treated with HindIII at 37° C. overnight, purified one more time, and yjeH and the BAC vector were cloned using T4 ligase. *E. coli* DH5a was transformed with the cloned plasmid, and the transformed *E. coli* DH5a was selected from LB plate medium containing chloramphenicol 50 µg/mL. The thus-prepared plasmid was introduced into W3-BTA and WCJM strains, which produce O-acetylhomoserine, and the flask evaluation on their O-acetylhomoserine productivity was performed.

The resulting PCR product was electrophoresed on a 1.0% agarose gel, and the DNA obtained from a 1.2 kb band was purified. The purified DNA was treated with HindIII at 37° C. overnight, purified one more time, and yjeH and the BAC vector were cloned using T4 ligase. *E. coli* DH5a was transformed with the cloned plasmid, and the transformed *E. coli* DH5a was selected from LB plate medium containing chloramphenicol 50 µg/mL and a plasmid was obtained therefrom. The thus-prepared plasmid was introduced into W3-BTA and WCJM strains, which produce O-acetylhomoserine, and the flask evaluation on their O-acetylhomoserine productivity was performed.

Specifically, each strain was spread on solid LB medium and cultured in a 33° C. incubator overnight. Single colonies for each strain cultured on solid LB medium overnight were inoculated to LB medium (3 mL), cultured at 33° C. for 5 hours. Again, the resultant was diluted 200-fold in a 250 mL Erlenmeyer flask containing 25 mL of medium for producing O-acetylhomoserine, cultured at 33° C. at a rate of 200 rpm for 30 hours, and the amount of O-acetylhomoserine production was confirmed by HPLC analysis. The results are summarized in Table 3 below.

TABLE 3

Measurement of O-acetylhomoserine production by flask culture

|  | OD (562 nm) | Glucose Consumption (g/L) | O-AH (g/L) |
|---|---|---|---|
| W3-BTA/pBAC | 9.5 | 35 | 0.8 |
| WCJM/pBAC | 9.6 | 35 | 1.2 |
| W3-BTA/pBAC-yjeH | 9.8 | 36 | 1.5 |
| WCJM/pBAC-yjeH | 10.1 | 37 | 2.3 |

As can be confirmed from Table 3, the introduction of the yjeH plasmid into the WCJM strain resulted in a higher OD value compared to that of the control strain, and also a higher rate of glucose consumption. The WCJM/pBAC-yjeH strain produced O-acetylhomoserine in a concentration of 2.3 g/L, thus confirming that the strain can have an increased O-acetylhomoserine productivity by the yjeH introduction.

Example 3: Preparation of a Plasmid with Enhanced yjeH Promoter and Evaluation of O-Acetylhomoserine Productivity 3-1. Preparation of a Plasmid with Enhanced yjeH Promoter An experiment was performed to replace the endogenous yjeH promoter with 3 different promoters having strong expression-inducing activities compared to that of the endogenous yjeH promoter, based on the plasmid prepared in Example 2.

Specifically, PCL vectors with promoters having an enhanced activity were prepared using pro, cysk, or icd promoter. The PCL vectors were prepared using the SmaI restriction site of the PCL vector, and the icd promoter (SEQ ID NO: 51) was prepared by PCR amplification using the primers of SEQ ID NOS: 39 and 40; the pro promoter (SEQ ID NO: 52) using the primers of SEQ ID NOS: 41 and 42; and the cysk promoter (SEQ ID NO: 53) using the primers of SEQ ID NOS: 43 and 44. The thus-prepared plasmids were introduced into the WCJM strain, respectively, and their O-acetylhomoserine productivities were evaluated in flasks.

Specifically, each strain was spread on LB plate medium and cultured in a 33° C. incubator overnight. Each strain cultured overnight on LB plate medium was inoculated into titer medium 25 mL and cultured in a 33° C. incubator at 200 rpm overnight. The results are shown in Table 4 below.

TABLE 4

Measurement of O-acetylhomoserine production by flask culture

|  | OD (562 nm) | Glucose Consumption (g/L) | O-AH (g/L) |
|---|---|---|---|
| WCJM/pCL1920 | 9.6 | 35 | 1.2 |
| WCJM/pCL-yjeH | 10.1 | 37 | 2.3 |
| WCJM/pCL-Picd-yjeH | 10.5 | 38 | 3.1 |
| WCJM/pCL-Ppro-yjeH | 10.7 | 38 | 3.5 |
| WCJM/pCL-Pcysk-yjeH | 9.4 | 39 | 4.4 |

As can be confirmed from Table 4, the strain introduced with the pCL-Pcysk-yjeH plasmid showed a decrease in OD value compared to that of the self-promoter, but the strain showed a higher rate of glucose consumption and the highest O-acetylhomoserine production (4.4 g/L).

3-2. Preparation of a Plasmid for Enhancing a Gene and Promoter in a Biosynthetic Pathway For maximizing O-acetylhomoserine productivity, a plasmid for enhancing the biosynthetic pathway up to homoserine was prepared. For cloning aspartate kinase, homoserine O-acetyltransferase, and yjeH into the PCL vector, the pCL-thrA-metX plasmid, which was already prepared, was used.

Specifically, for obtaining the yjeH gene, PCR was performed using the primers (SEQ ID NOS: 11 and 12) for a total of 30 cycles under the following conditions: denaturation at 94° C. for 30 sec, annealing at 55° C. for 30 sec, and extension at 68° C. for 1 min.

The resulting PCR product was electrophoresed on a 1.0% agarose gel, and the DNA obtained from a 1.2 kb band was purified. The purified DNA was treated with KpnI at 37° C. overnight, purified one more time, and yjeH and the BAC vector were cloned using T4 ligase. *E. coli* DH5α was transformed with the cloned plasmid, and the transformed *E. coli* DH5a was selected from LB plate medium containing spectinomycin 50 μg/mL and plasmid was obtained therefrom. The thus-prepared plasmid was introduced into the WCJM strain, which produces O-acetylhomoserine, and the flask evaluation on their O-acetylhomoserine productivity was performed. The thus-prepared plasmids were all 3 kinds and they were prepared using the 3 different promoters prepared in Example 3-1. The 3 different kinds of plasmids were introduced into the WCJM strain and the flask evaluation was performed in the same manner as in Example 3-1. The results are shown in Table 5 below.

TABLE 5

Measurement of O-acetylhomoserine production by flask culture

|  | OD (562 nm) | Glucose Consumption (g/L) | O-AH (g/L) |
| --- | --- | --- | --- |
| WCJM/pC2 | 9.6 | 35 | 1.5 |
| WCJM/pC2-yjeH | 10.1 | 37 | 2.8 |
| WCJM/pC2-Picd-yjeH | 10.5 | 38 | 4.2 |
| WCJM/pC2-Ppro-yjeH | 10.7 | 38 | 4.5 |
| WCJM/pC2-Pcysk-yjeH | 9.4 | 39 | 5.4 |

As can be confirmed from Table 5, when the biosynthetic pathway and yjeH were enhanced simultaneously, the O-acetylhomoserine production was improved further. The order of the increase of the O-acetylhomoserine production was as follows: in the same manner as described above, the strain introduced with the pC2-Pcysk-yjeH plasmid showed a decrease in OD value compared to that of the strain, in which the self-promoter was used, but the strain introduced with the pC2-Pcysk-yjeH plasmid showed the highest glucose consumption rate, and also the highest O-acetylhomoserine production (5.4 g/L).

Example 4: Preparation of a Strain with Enhanced Endogenous yjeH Promoter and Evaluation of O-Acetylhomoserine Productivity 4-1. Preparation of a Strain with Enhanced Endogenous yjeH and Evaluation Thereof For preparing a strain with an enhanced activity of the endogenous yjeH gene of the WCJM strain, which produces O-acetylhomoserine, an experiment of replacing a promoter was performed. The WCJM strain of the present disclosure has one copy of the yjeH gene, and the strain was prepared to increase the yjeH gene by enhancing the promoter instead of increasing the copy number of the yjeH gene.

Specifically, as a promoter for the replacement, the icd, cysK, and pro promoters (Picd, Pcysk, and Ppro), whose activities were confirmed in Example 3, and the FRT one-step PCR deletion method specified above was used (Wanner B L., *Proc. Natl. Acad. Sci. USA* 97: 6640-6645, 2000). Insertion cassettes were prepared using the pKD4 vector as a template along with the primers of SEQ ID NOS: 45 and 46 for the icd promoter, the primers of SEQ ID NOS: 47 and 48 for the cysk promoter, and the primers of SEQ ID NOS: 49 and 50 for the pro promoter. PCR was performed for a total of 30 cycles under the following conditions: denaturation at 94° C. for 30 sec, annealing at 55° C. for 30 sec, and extension at 72° C. for 1 min.

The thus-obtained PCR product was electrophoresed on a 1.0% agarose gel, and the DNA obtained from a 2.5 kb band was purified. The recovered DNA fragment was introduced into the WCJM strain, which was already transformed with the pKD46 vector (Wanner B L., *Proc. Natl. Acad. Sci. USA* 97: 6640-6645, 2000), by electroporation. The WCJM strain transformed with pKD46 was cultured using LB medium containing ampicillin 100 μg/L and L-arabinose 5 mM until the culture reached an $OD_{600}=0.6$ at 30° C., and used after washing twice with sterile distilled water and once with 10% glycerol. The electroporation was performed at 2500 V. The recovered strain was spread on LB plate medium containing chloramphenicol 25 μg/L, cultured overnight at 37° C., and the resistant strains were selected.

PCR was performed using the thus-selected strain as a template along with the primers of SEQ ID NOS: 45 and 46 for the icd promoter, the primers of SEQ ID NOS: 47 and 48 for the cysk promoter, and the primers of SEQ ID NOS: 49 and 50 for the pro promoter under the same conditions described above, and the replacement of the endogenous promoter of the yjeH gene with each of the foreign promoter was confirmed by observing the presence of a 2.5 kb gene band on a 1.0% agarose gel. The strains, in which the promoter replacement was confirmed, were transformed with the pCP20 vector (Wanner B L., *Proc. Natl. Acad. Sci. USA* 97: 6640-6645, 2000) and cultured in LB medium. Then, PCR was performed under the same conditions followed by electrophoresis on a 1.0% agarose gel to prepare the final strains with the promoter replacement represented by the gene band, which was reduced to a size of 1 kb, thereby confirming the removal of the kanamycin marker from the strains. The thus-prepared strains were named according to their respective promoter: i.e., "WCJM-PIY" for the strain with the icd replaced promoter of icd, "WCJM-PCY" for the strain with the replaced promoter of cysk, and "WCJM-PCY" for the strain with the replaced promoter of pro. The O-acetylhomoserine productivities of the strains, in which the promoter of the yjeH gene was replaced, were measured by performing flask culture evaluation and the results are shown in Table 6 below.

TABLE 6

Measurement of O-acetylhomoserine production by flask culture

|  | OD (562 nm) | Glucose Consumption (g/L) | O-AH (g/L) |
| --- | --- | --- | --- |
| WCJM | 9.6 | 35 | 1.2 |
| WCJM-PIY | 9.2 | 38 | 1.8 |
| WCJM-PCY | 10.5 | 38 | 3.1 |
| WCJM-PPY | 10.1 | 38 | 1.9 |

As can be confirmed from Table 6, when the yjeH gene expression of the WCJM strain was enhanced by replacing the endogenous promoter of the yjeH gene within the chromosome with a promoter having a strong expression activity, the O-acetylhomoserine productivity was not rapidly changed compared to the result of Example 3, in which the strain was transformed by introducing with a plasmid (5 copies), but the O-acetylhomoserine productivity of each of the strains was shown to increase compared to that of the WCJM strain, which is the strain producing O-acetylhomoserine.

4-2. Preparation of a Strain with an Enhanced Promoter of the yjeH Gene in a Strain with a High Yield of O-Acetylhomoserine and Evaluation of O-Acetylhomoserine Productivity of the Strain The method of preparing a strain producing O-acetylhomoserine using a wild-type W3110-derived strain, which has threonine productivity by NTG mutation, is known (International Publication No. WO 2012/087039). In particular, the thus-prepared strain producing O-acetylhomoserine in high yield was deposited at Korean Culture Center of Microorganisms (KCCM) with Accession No. KCCM11468P.

The strain with Accession No. KCCM11146P has high-yield O-acetylhomoserine productivity, which consumes 40 g/L of glucose and produces about 15 g/L to 16 g/L during flask culture. In this regard, the present inventors examined whether the strains, which already have high O-acetylhomoserine productivity, can further improve their O-acetylhomoserine productivity by enhancing the yjeH gene in the strains.

Specifically, the promoter of the yjeH gene was replaced with a promoter with a high expression-inducing activity, and this was performed in the same manner as in Example 4-1. The thus-prepared strains, in which the promoter of the yjeH gene of the KCCM11146P strain, were named as "KCCM11146P-PIY" for the strain with the replaced promoter of icd, "KCCM11146P-PCY" for the strain with the replaced promoter of cysk, and "KCCM11146P-PPY" for the strain with the replaced promoter of pro, respectively.

The O-acetylhomoserine productivities of the strains, in which the promoter of the yjeH gene was replaced, were measured by flask culture evaluation. Specifically, KCCM11146P, KCCM11146P-PIY, KCCM11146P-PCY, and KCCM11146P-PPY strains were inoculated into LB medium and cultured at 33° C. overnight. The resulting single colonies were inoculated into 3 mL of LB medium, cultured at 33° C. for 5 hours, diluted 200-fold in a 250 mL Erlenmeyer flask containing 25 mL of medium for producing O-acetylhomoserine, cultured at 33° C. for at a rate of 200 rpm for 30 hours, and the amount of O-acetylhomoserine production was analyzed by HPLC. The results are shown in Table 7 below.

TABLE 7

Measurement of O-acetylhomoserine production by flask culture

|  | OD (562 nm) | Glucose Consumption (g/L) | O-AH (g/L) |
| --- | --- | --- | --- |
| KCCM11146P | 18.3 | 40 | 14.2 |
| KCCM11146P-PIY | 16.2 | 40 | 16.3 |
| KCCM11146P-PCY | 19.2 | 40 | 18.2 |
| KCCM11146P-PPY | 18.8 | 40 | 16.2 |

As can be confirmed from Table 7, the KCCM11146P strain produced 14.2 g/L of O-acetylhomoserine, whereas, in the cases of the strains with a replaced promoter, the PCY strain showed the highest production (18.2 g/L) and the PIY and PPY strains showed an increased production of O-acetylhomoserine compared to that of the original strain.

The present inventors have confirmed that the strain based on the KCCM11146P strain, in which the yjeH gene activity is enhanced, can increase O-acetylhomoserine production. As a result, the inventors have named the strain as "CA05-4008", and deposited the strain with the Korean Culture Center of Microorganisms (KCCM), under the Budapest Treaty, on Nov. 22, 2013, with Accession No. KCCM11484P.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A modified microorganism of the genus *Escherichia* producing O-acetylhomoserine, wherein an activity of the protein comprising the amino acid sequence of SEQ ID NO: 1 in a microorganism of the genus *Escherichia* capable of producing O-acetylhomoserine is enhanced compared to a non-modified microorganism;
    wherein an activity of cystathionine synthase is weakened or inactivated compared to a non-modified microorganism; and
    wherein an activity of homoserine acetyltransferase is further enhanced compared to a non-modified microorganism.

2. The modified microorganism of the genus *Escherichia* according to claim 1, wherein the microorganism is *Escherichia coli*.

3. The modified microorganism of the genus *Escherichia* according to claim 1, wherein an activity of homoserine kinase is further weakened or inactivated.

4. The modified microorganism of the genus *Escherichia* according to claim 1, wherein the activity of at least one enzyme selected from the group consisting of phosphoenolpyruvate carboxylase, aspartate aminotransferase, and aspartate semialdehyde dehydrogenase is further enhanced.

5. The modified microorganism of the genus *Escherichia* according to claim 1, wherein an activity of aspartate kinase is enhanced compared to a non-modified microorganism.

6. A method for producing O-acetylhomoserine comprising culturing the modified microorganism of the genus *Escherichia* producing O-acetylhomoserine of claim 1 to obtain a cultured medium.

7. The method according to claim 6, further comprising recovering O-acetylhomoserine from the cultured microorganism or the cultured medium.

8. A method for producing L-methionine, comprising:
    culturing a modified microorganism of the genus *Escherichia* producing O-acetylhomoserine of claim 1 thereby accumulating O-acetylhomoserine; and
    producing L-methionine from the accumulated O-acetylhomoserine by using an enzyme reaction.

* * * * *